(12) United States Patent
Lee et al.

(10) Patent No.: US 12,427,525 B2
(45) Date of Patent: Sep. 30, 2025

(54) GENE AMPLIFICATION MODULE

(71) Applicant: LG Chem, Ltd., Seoul (KR)

(72) Inventors: Sang Hun Lee, Daejeon (KR); Chang Ju Park, Daejeon (KR); Se Ryun Kim, Daejeon (KR); Hoon Sung Jeh, Daejeon (KR); Jae Hoon Oh, Daejeon (KR)

(73) Assignee: Invitros Co., Ltd., Seoul (KR)

( * ) Notice: Subject to any disclaimer, the term of this patent is extended or adjusted under 35 U.S.C. 154(b) by 1092 days.

(21) Appl. No.: 17/423,291

(22) PCT Filed: Jan. 7, 2020

(86) PCT No.: PCT/KR2020/000289
§ 371 (c)(1),
(2) Date: Jul. 15, 2021

(87) PCT Pub. No.: WO2020/149559
PCT Pub. Date: Jul. 23, 2020

(65) Prior Publication Data
US 2022/0080426 A1    Mar. 17, 2022

(30) Foreign Application Priority Data
Jan. 17, 2019    (KR) .................. 10-2019-0006143

(51) Int. Cl.
*B01L 7/00*       (2006.01)
*C12Q 1/6844*     (2018.01)

(52) U.S. Cl.
CPC ......... *B01L 7/52* (2013.01); *B01L 2300/0858* (2013.01); *B01L 2300/1805* (2013.01); *B01L 2300/1894* (2013.01); *C12Q 1/6844* (2013.01)

(58) Field of Classification Search
CPC ....... B01L 7/52; B01L 7/00; B01L 2300/1822
See application file for complete search history.

(56) References Cited

U.S. PATENT DOCUMENTS

| 4,865,986 A | 9/1989 | Coy et al. |
| 4,950,608 A | 8/1990 | Kishimoto |

(Continued)

FOREIGN PATENT DOCUMENTS

| CN | 101155641 | 4/2008 |
| CN | 103649300 | 3/2014 |

(Continued)

OTHER PUBLICATIONS

International Search Report for Application No. PCT/KR2020/000289 mailing Apr. 14, 2020, 2 pages.

(Continued)

*Primary Examiner* — Natalia Levkovich
(74) *Attorney, Agent, or Firm* — Lerner David LLP (57) ABSTRACT

A gene amplification module is disclosed.
According to one aspect of the present invention, provided is a gene amplification module including: a heat block in which a reaction container accommodation space is defined; a heating part provided below the heat block; a cooling part provided below the heating part; and a fluid supply part provided to face one side of the heat block, the fluid supply part being configured to supply a cooling fluid to the heat block, wherein sidewalls defining a circumference of the heat block are provided on the heat block, and one or more supply holes configured to supply the cooling fluid are defined in the sidewalls.

8 Claims, 6 Drawing Sheets

(56) References Cited

U.S. PATENT DOCUMENTS

| | | |
|---|---|---|
| 5,475,610 A | 12/1995 | Atwood et al. |
| 5,602,756 A | 2/1997 | Atwood et al. |
| 5,710,381 A | 1/1998 | Atwood et al. |
| 6,015,534 A | 1/2000 | Atwood |
| 6,337,435 B1 | 1/2002 | Chu et al. |
| 2002/0030044 A1 | 3/2002 | Brown |
| 2003/0152492 A1 | 8/2003 | Chang et al. |
| 2004/0152122 A1 | 8/2004 | Hwang et al. |
| 2005/0000231 A1* | 1/2005 | Lee .................. F25B 21/04 62/3.5 |
| 2005/0002024 A1 | 1/2005 | Green |
| 2006/0166226 A1 | 7/2006 | Kudoh et al. |
| 2007/0026421 A1 | 2/2007 | Sundberg et al. |
| 2007/0110634 A1 | 5/2007 | Heimberg et al. |
| 2007/0140926 A1 | 6/2007 | Heimberg et al. |
| 2007/0169488 A1 | 7/2007 | Oh et al. |
| 2007/0184548 A1* | 8/2007 | Tan .................. B01L 7/52 435/303.1 |
| 2008/0248534 A1 | 10/2008 | Lim et al. |
| 2009/0203082 A1 | 8/2009 | Schlaubitz et al. |
| 2009/0263782 A1 | 10/2009 | Ward et al. |
| 2009/0269835 A1 | 10/2009 | Ceremony et al. |
| 2010/0120099 A1 | 5/2010 | Heimberg et al. |
| 2010/0120100 A1 | 5/2010 | Heimberg et al. |
| 2010/0203595 A1 | 8/2010 | Ward et al. |
| 2010/0285536 A1 | 11/2010 | Hwang et al. |
| 2011/0129914 A1 | 6/2011 | Schlaubitz et al. |
| 2011/0152108 A1 | 6/2011 | Brenan et al. |
| 2011/0312102 A1 | 12/2011 | Jo |
| 2012/0021463 A1 | 1/2012 | Hwang et al. |
| 2012/0077262 A1 | 3/2012 | Takei et al. |
| 2012/0240597 A1 | 9/2012 | Hong et al. |
| 2012/0264206 A1 | 10/2012 | Heimberg et al. |
| 2012/0288865 A1 | 11/2012 | Sundberg et al. |
| 2013/0137144 A1 | 5/2013 | Chu et al. |
| 2013/0143272 A1 | 6/2013 | Guo et al. |
| 2014/0030170 A1 | 1/2014 | Heimberg et al. |
| 2014/0093879 A1 | 4/2014 | Knight et al. |
| 2014/0170707 A1 | 6/2014 | Hwang et al. |
| 2014/0208772 A1 | 7/2014 | Schon et al. |
| 2014/0248690 A1 | 9/2014 | Takei et al. |
| 2014/0311706 A1 | 10/2014 | Tenzler et al. |
| 2015/0283541 A1 | 10/2015 | Curran et al. |
| 2016/0377562 A1 | 12/2016 | Sundberg et al. |
| 2018/0111118 A1 | 4/2018 | Curran et al. |
| 2018/0154363 A1 | 6/2018 | Figley et al. |
| 2018/0321170 A1 | 11/2018 | Knight et al. |
| 2019/0070611 A1 | 3/2019 | Schlaubitz et al. |
| 2019/0329261 A1 | 10/2019 | Won et al. |
| 2022/0168744 A1 | 6/2022 | Schlaubitz et al. |

FOREIGN PATENT DOCUMENTS

| | | |
|---|---|---|
| CN | 103781550 A | 5/2014 |
| CN | 105586403 A | 5/2016 |
| EP | 1157744 A1 | 11/2001 |
| JP | H05168459 A | 7/1993 |
| JP | H06233670 A | 8/1994 |
| JP | H08117590 A | 5/1996 |
| JP | 2003505663 A | 2/2003 |
| JP | 2006238759 A | 9/2006 |
| JP | 4464869 B2 | 5/2010 |
| JP | 4477089 B2 | 6/2010 |
| JP | 2011250800 A | 12/2011 |
| JP | 2015535429 A | 12/2015 |
| KR | 20020017212 A | 3/2002 |
| KR | 20020038765 A | 5/2002 |
| KR | 20070118683 A | 12/2007 |
| KR | 20090042002 A | 4/2009 |
| KR | 20120107716 A | 10/2012 |
| KR | 20140134435 A | 11/2014 |
| KR | 20180090955 A | 8/2018 |
| KR | 102009505 B1 | 8/2019 |
| WO | 2008035074 A2 | 3/2008 |
| WO | 2009054647 A2 | 4/2009 |
| WO | 2014185628 | 11/2014 |

OTHER PUBLICATIONS

Extended European Search Report and European Search Opinion for European Patent Application No. 20740902 dated Jan. 25, 2022, 8 pgs.

* cited by examiner

GENE AMPLIFICATION MODULE

CROSS-REFERENCE TO RELATED APPLICATION

This application is a national phase entry under 35 U.S.C. § 371 of International Application No. PCT/KR2020/000289, filed on Jan. 7, 2020, which claims priority to Korean Patent Application No. 10-2019-0006143, filed on Jan. 17, 2019, the contents of which are hereby incorporated herein by reference in their entireties.

TECHNICAL FIELD

The present invention relates to a gene amplification module that is capable of quickly heating and cooling a specimen within a reaction container when compared to the prior art.

BACKGROUND ART

A gene amplification module for nucleic acid amplification (or polymerase chain reaction) is essential for genetic diagnosis to obtain various biological information in a specimen. That is, when the gene is diagnosed, a specific gene within the specimen collected by the gene amplification module is amplified to increase in number of genes within the specimen, and then, a degree of amplification of the specific gene is confirmed to obtain desired biological information.

The gene amplification is performed by repeatedly adjusting a temperature. More particularly, the specimen periodically increases and descends in temperature at regular time intervals to amplify the gene of the specimen.

However, according to the related art, there is a limit in realizing high speed of the gene amplification due to a long period of the temperature increase and decrease in the gene amplification module. Particularly, according to the related art, when the temperature of the specimen is periodically adjusted in the gene amplification module, there is a problem that a cooling rate is slower than a heating rate. This causes a problem that a time taken to amplify the gene of the specimen increases. Ultimately, a time taken to diagnose the gene increases.

DISCLOSURE OF THE INVENTION

Technical Problem

An object of the present invention for solving the above problem is to reduce a time taken to amplify a gene of a specimen so as to reduce a time taken to diagnose the gene.

Technical Solution

According to one aspect of the present invention for achieving the above object, provided is a gene amplification module including: a heat block in which a reaction container accommodation space for accommodating a reaction container containing a specimen to be amplified is defined; a heating part provided below the heat block to heat the heat block by being heat-exchanged with the heat block through thermal conduction; a cooling part provided below the heating part to cool the heat block by being heat-exchanged with the heating part through thermal conduction; a fluid supply part provided to face one side of the heat block, the fluid supply part being configured to supply a cooling fluid to the heat block, wherein sidewalls defining a circumference of the heat block are provided on the heat block, and one or more supply holes configured to supply the cooling fluid are defined in the sidewalls.

An empty space may be defined in the heat block, and the empty space may communicate with the supply holes.

In the heat block, total m×n reaction container accommodation spaces may be defined in an m×n matrix form (where m and n are natural numbers different from each other), or total $n^2$ reaction container accommodation spaces may be defined in an n×n matrix form, and the supply holes may be defined between the reaction container accommodation spaces, respectively.

The fluid supply part may include: a first fluid supply part provided to face the sidewall of the heat block in which the supply holes are defined; and a second fluid supply part provided to face the other sidewall of the heat block in which the supply holes are defined.

The fluid supply part may be provided in close contact with the sidewall, in which the supply holes are defined, among the sidewalls.

The empty space may be spaced apart from the reaction container accommodation space.

The empty space may include: a first empty space communicating with the supply holes; and a second empty space defined to cross the first empty space.

Discharge holes communicating with the second empty space may be defined in the sidewalls of the heat block.

The discharge holes may be defined in both ends of the second empty space, respectively.

The fluid supply part may include a rotatable fan to allow the cooling fluid to be supplied into the empty space of the heat block.

Advantageous Effects

According to the present invention, the method for cooling the specimen may be additionally performed to increase in cooling speed when compared to the method according to the related art. Thus, the time taken to amplify the gene of the specimen may be reduced to reduce the time taken to diagnose the gene.

MODE FOR CARRYING OUT THE INVENTION

Hereinafter, a structure of a gene amplification module according to the present invention will be described with reference to the accompanying drawings.

Gene Amplification Module

Figure 1:
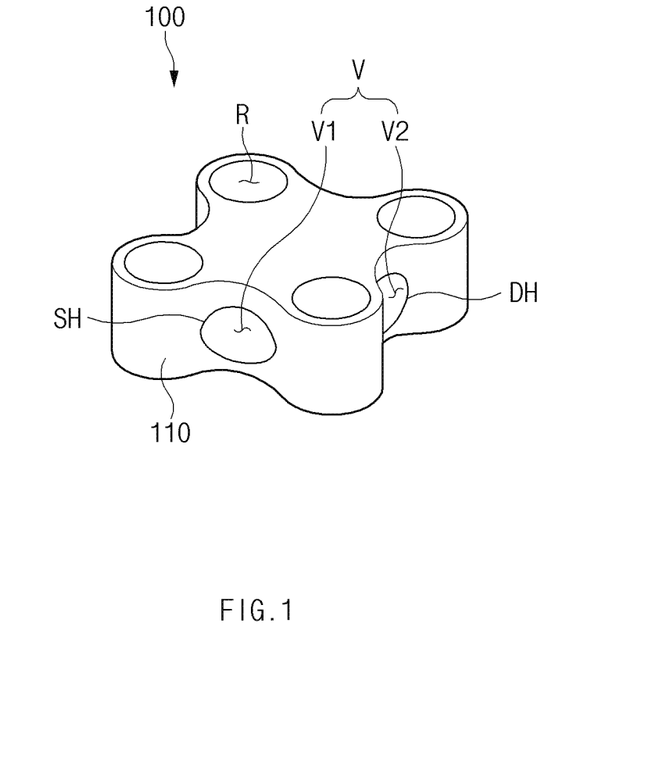
FIG. 1 is a perspective view illustrating an example of a structure of a heat block of a gene amplification module according to the present invention.
Figure 2:
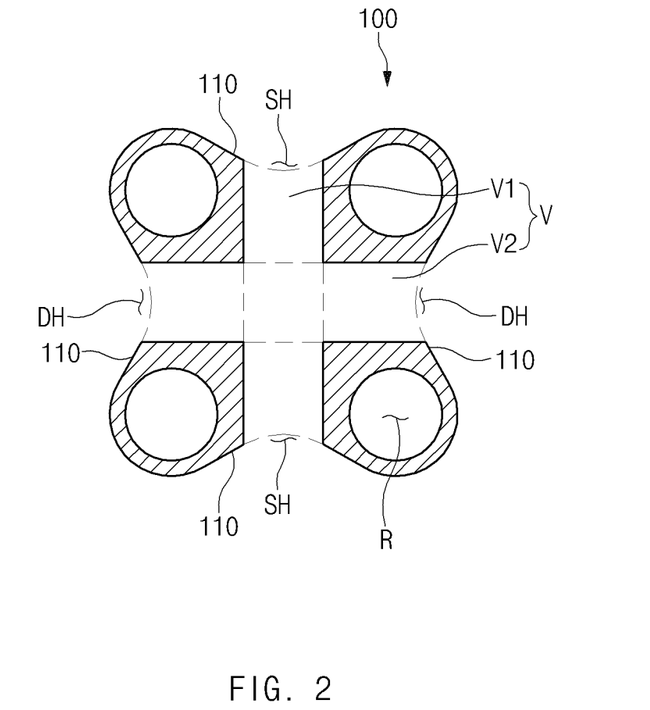
FIG. 2 is a horizontal cross-sectional view illustrating an example of the structure of the heat block of the gene amplification module according to the present invention.
Figure 3:
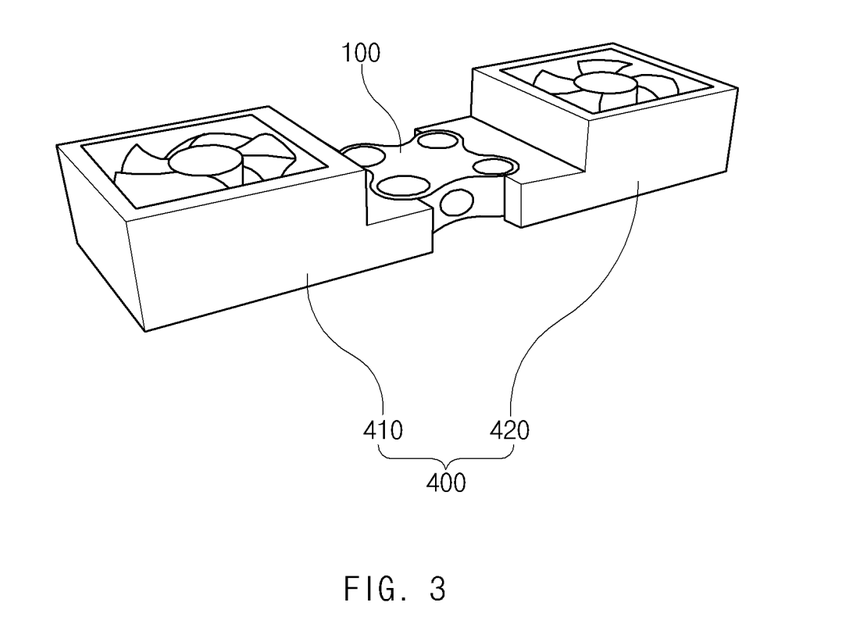
FIG. 3 is a perspective view illustrating a coupling relationship between the heat block and a fluid supply part in the gene amplification module according to the present invention.

FIG. 1 is a perspective view illustrating an example of a structure of a heat block of a gene amplification module according to the present invention, and FIG. 2 is a horizontal cross-sectional view illustrating an example of the structure of the heat block of the gene amplification module according to the present invention. FIG. 3 is a perspective view illustrating a coupling relationship between the heat block and a fluid supply part in the gene amplification module according to the present invention.

As illustrated in FIG. 1, a gene amplification module according to the present invention may include a heat block 100.

The heat block 100 may be configured to accommodate a specimen to be amplified. The specimen may be periodically heated and cooled by heat transfer of the heat block 100 to amplify a gene of the specimen accommodated in the heat block 100. In order to efficiently transfer heat during the heating and cooling, the heat block 100 may be made of a material having high thermal conductivity such as gold, silver, copper, an alloy, aluminum, and the like. For example, the heat block 100 may be made of aluminum.

For this, as illustrated in FIG. 1, a reaction container accommodation space R for accommodating a reaction container (not shown) in which a specimen to be amplified is provided may be defined in the heat block 100. FIG. 1 illustrates a case in which total four reaction container accommodation spaces R are defined in the heat block 100 in a 2×2 matrix form. However, the number or arrangement of the reaction container accommodation spaces R are not limited to the structure of FIG. 1. The reaction container may be made of a plastic material.

Sequentially, referring to FIG. 1, a sidewall 110 defining a circumference of the heat block 100 may be disposed on the heat block 100. FIG. 1 illustrates a case in which four sidewalls, each of which has a curved surface having a wave shape, are provided. When each of the sidewalls of the heat block 100 has the curved surface having the wave shape, the heat block 100 may be minimized in weight to reduce heat capacity thereof, thereby minimizing heating and cooling rates thereof when compared to a case in which four planes meet each other to form the sidewalls of the heat block. However, each of the sidewalls defining a circumference of the heat block 100 according to the present invention may have various shapes in addition to the wave shape. That is, the shape of the sidewall of the heat block 100 according to the present invention is not limited to the wave shape.

At least one or more holes may be defined in the sidewalls of the heat block 100. The holes defined in the heat block 100 may be configured to supply and discharge a cooling fluid for cooling the heated heat block 100. As illustrated in FIGS. 1 and 2, a supply hole SH to which the cooling fluid is supplied may be defined in a portion of the sidewalls 110 of the heat block 100, and a discharge hole DH through which the cooling fluid is discharged to the outside may be defined in the other portion of the sidewalls 110 of the heat block 100. Here, the cooling fluid may be air a gas. For example, the cooling fluid may be air at room temperature.

Sequentially, referring to FIG. 2, an empty space V may be defined in the heat block 100. The empty space V may communicate with the supply hole SH and the discharge hole DH. Thus, the empty space V may provide a path through which the cooling fluid supplied to the heat block 100 flows.

Two supply holes SH may be provided. Here, the supply holes SH may be defined at sides opposite to each other with the empty space V therebetween.

As illustrated in FIG. 2, the empty space V defined in the heat block 100 may do not communicate with the reaction container accommodation space R but be spaced apart from the reaction container accommodation space R.

As described above, the reaction container containing the specimen to be amplified may be accommodated in the reaction container accommodation space R. When the reaction container accommodation space R and the empty space V communicate with each other, an inner wall defining the reaction container accommodation space R may not sufficiently surround the reaction container. In this case, since the specimen is not quickly heated or cooled by the heat block 100, a time taken to amplify the specimen increases. Thus, according to the present invention, it is preferable that the reaction container accommodation space R does not communicate with the empty space V so that the specimen is quickly heated or cooled by the heat block 100.

In addition, as illustrated in FIG. 2, the empty space V defined in the heat block 100 may include a first empty space V1 and a second empty space V2. Among them, the first empty space V1 may have both ends which are respectively connected to the supply holes SH. In addition, the second empty space V2 may defined to cross the first empty space V1.

Also, holes may be further defined in the sidewalls of the heat block 100 in addition to the supply holes SH. That is, as illustrated in FIG. 2, discharge holes DH may be further defined in the sidewalls of the heat block 100. FIG. 2 illustrates a case in which the discharge holes DH are respectively defined one by one in the sidewalls disposed at left and right sides of the heat block 100. The discharge holes DH may communicate with the second empty space V2. Also, the discharge hole DH may also be provided in plurality. For example, as illustrated in FIG. 2, the discharge holes DH may be defined in both ends of the second empty space V2.

As illustrated in FIG. 3, the gene amplification module according to the present invention may further include a fluid supply part 400 disposed to face one of the sidewalls of the heat block 100 and supply the cooling fluid to the heat block 100. The fluid supply part 400 may face the sidewall in which the supply hole SH (see FIG. 2) is defined. Thus, the fluid supply part 400 may supply the cooling fluid to the empty space V (see FIG. 2) within the heat block 100 through the supply hole.

Sequentially, referring to FIG. 3, the fluid supply part 400 of the gene amplification module according to the present invention may be provided in plurality. The fluid supply part 400 may be provided as many as the number of supply holes SH (see FIG. 2). FIG. 3 illustrates a first fluid supply part 410 disposed to face the sidewall of the heat block 100, in which one of the two supply holes defined in the heat block 100 is defined, and a second fluid supply part 420 disposed to face the sidewall of the heat block 100, in which the other one of the two supply holes defined in the heat block 100 is defined.

The fluid supply part 400 according to the present invention may include a rotatable fan so that the cooling fluid is supplied to the empty space of the heat block 100.

As illustrated in FIG. 3, the fluid supply part 400 may be disposed in close contact with the sidewall in which the supply hole SH (see FIG. 2) is defined. Thus, leakage of the cooling fluid from the fluid supply part 400 to other portions except for the heat block 100 may be minimized.

As described above, the supply hole SH (see FIG. 2) and the discharge hole DH (see FIG. 2) may be defined in the heat block 100. Here, the gene amplification module may further include a fluid discharge part (not shown) that is disposed to face the discharge hole and discharges the cooling fluid within the heat block 100 to the outside through the discharge hole.

Figure 4:
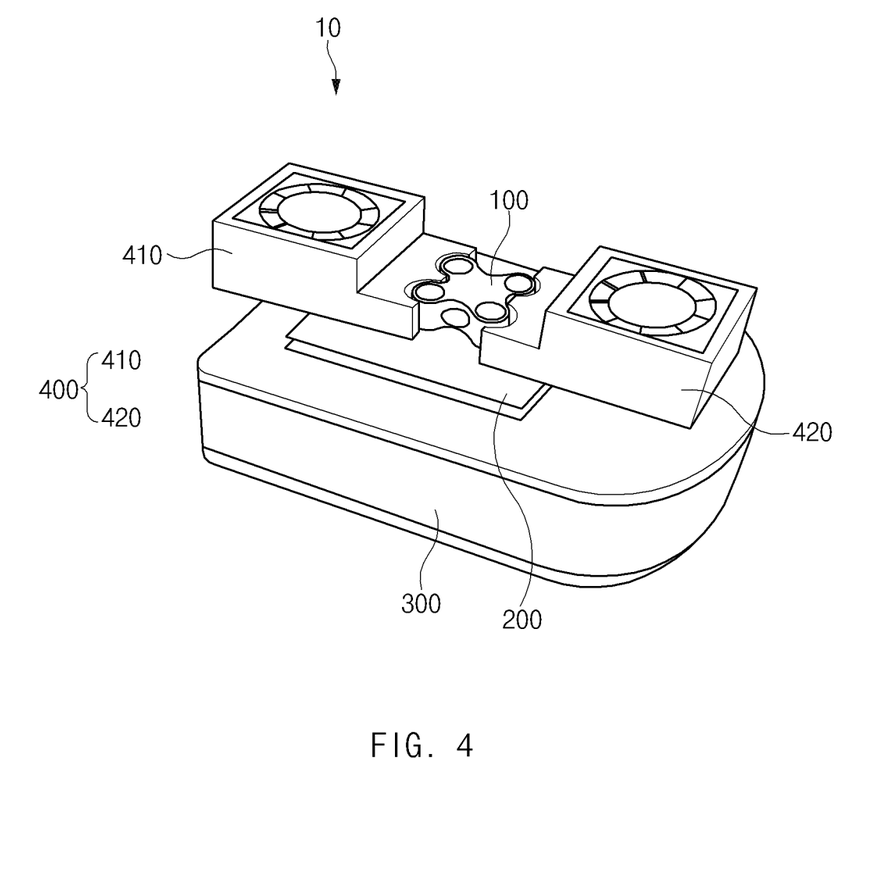
FIG. 4 is a perspective view illustrating a structure of the gene amplification module according to the present invention.

FIG. 4 is a perspective view illustrating a structure of the gene amplification module according to the present invention.

As described above, the gene amplification module 10 according to the present invention may include the heat block and the fluid supply part 400.

Also, the gene amplification module 10 according to the present invention may include a heating part 200 that is provided below the heat block 200 to heat the heat block 100. The heat part 200 may contact the heat block 100. Thus, the heating part 200 may be heat-exchanged with the heat block 100 through heat conduction. The heating part 200 according to the present invention may be configured to the heat block 100 by a local temperature increase due to the Peltier effect.

The Peltier effect refers to a phenomenon in which a temperature difference occurs at both sides due to movement of thermal energy together with current when a voltage is applied to both the sides of an object. The heating part according to the present invention may be configured to heat the heat block through the Peltier effect.

Sequentially, referring to FIG. 4, the gene amplification module according to the present invention may further include a cooling part 300 disposed below the heating part 200 to cool the heat block 100. The cooling part 300 may contact the heating part 200. Thus, the cooling part 300 may cool the heat block 100 by heat-exchange between the cooling part 300 and the heating part 200 through thermal conduction and heat-exchange between the heating part 200 and the heat block 100. That is, the cooling part 300 according to the present invention may be a heat sink having a lower temperature and a significantly higher heat capacity than the heat block 100 and the heating part 200.

Hereinafter, an operation method of the gene amplification module according to the present invention on the basis of the above description and drawings will be described as follows.

When the reaction container containing a specimen within the reaction container accommodation space R of the heat block 100 is disposed, and then, the heating part 200 operates to increase in temperature thereof, the heat block 100 may increase in temperature by the heat-exchange between the heat block 100 and the heating part 200 through the thermal conduction, and thus, the specimen within the reaction container may also increase in temperature.

When the temperature of the specimen reaches a predetermined value, the operation of the heating part 200 is stopped. Thus, the heat block 100 may decrease in temperature by the heat-exchange between the cooling part 300 and the heating part 200 through the thermal conduction and the heat-exchange between the heating part 200 and the heat block 100 through the thermal conduction, and thus, the specimen within the reaction container may also decrease in temperature.

Particularly, according to the present invention, since the cooling fluid is supplied to the empty space V of the heat block 100 through the supply hole SH of the heat block 100 through the fluid supply part 400 together with the operation of the cooling part 300, the cooling fluid may additionally cool the heat block 100. Therefore, the heat block 100 and the specimen may be more quickly cooled to significantly reduce the overall time required for the amplification process of the specimen.

Figure 5:
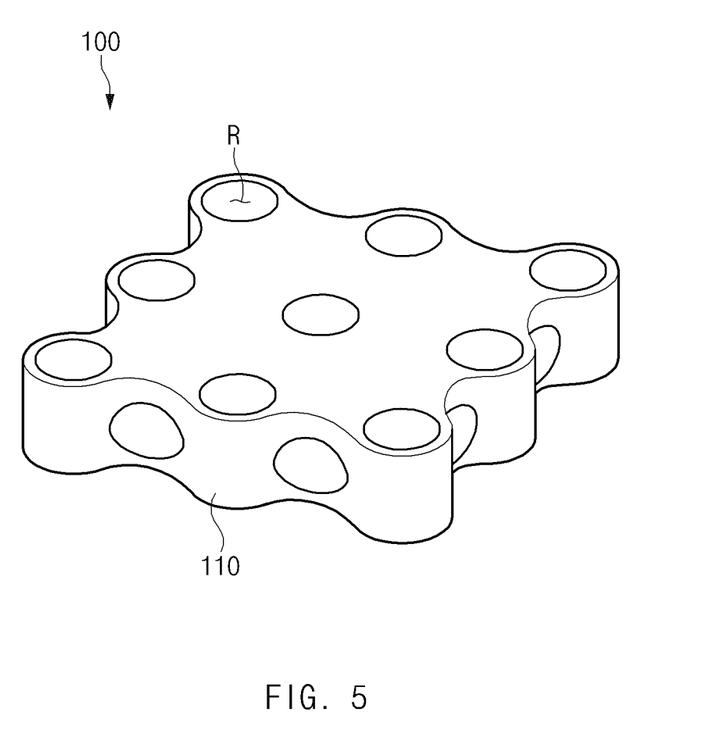
FIG. 5 is a perspective view illustrating another example of the structure of the heat block of the gene amplification module according to the present invention.
Figure 6:
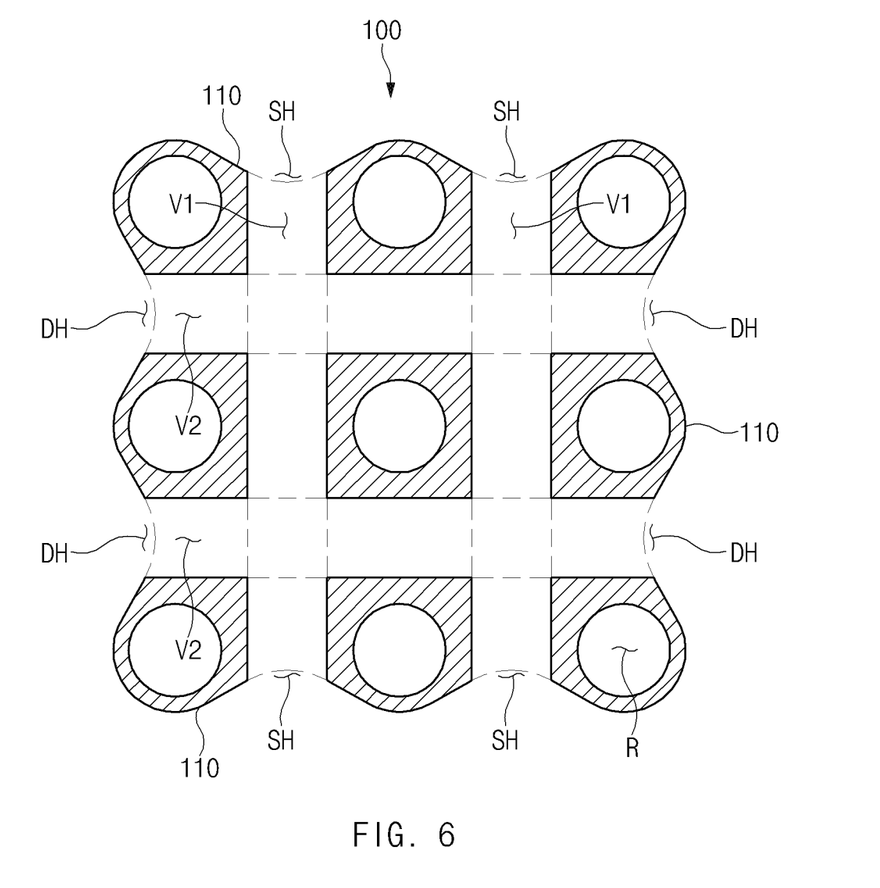
FIG. 6 is a horizontal cross-sectional view illustrating another example of the structure of the heat block of the gene amplification module according to the present invention.

FIG. 5 is a perspective view illustrating another example of the structure of the heat block of the gene amplification module according to the present invention, and FIG. 6 is a horizontal cross-sectional view illustrating another example of the structure of the heat block of the gene amplification module according to the present invention.

As described above, in the heat block according to the present invention, total four reaction container accommodation spaces may be defined in a 2×2 matrix form. However, the heat block may have a different structure. For example, as illustrated in FIGS. 5 and 6, in the heat block 100 of the gene amplification module according to the present invention, total nine reaction container accommodation spaces R may be defined in a 3×3 matrix form. Alternatively, in the heat block 100, total nine reaction container accommodation spaces R may be defined in a 4×4 matrix form. In general, in the heat block 100 of the gene amplification module according to the present invention, total $n^2$ reaction container accommodation spaces may be defined in an n×n matrix form.

Alternatively, in the heat block of the gene amplification module according to the present invention, total m×n reaction container accommodation spaces may be defined in an m×n matrix form (where m and n are natural numbers different from each other). For example, in the heat block, total six reaction container accommodation spaces may be defined in a 2×3 matrix form.

Sequentially, referring to FIGS. 5 and 6, a plurality of supply holes SH and discharge holes DH may be defined in the sidewalls defining the circumference of the heat block 100. For example, as illustrated in FIG. 6, when total nine reaction container accommodation spaces R are defined in a 3×3 matrix form in the heat block 100, two supply holes SH may be defined in each of two sidewalls defined at opposite sides with the first empty space V1, which is defined in the heat block 100, therebetween, and thus, total four supply holes SH may be defined in the heat block 100. Similarly, as illustrated in FIG. 6, when total nine reaction container accommodation spaces R are defined in a 3×3 matrix form in the heat block 100, two discharge holes DH may be defined in each of two sidewalls defined at opposite sides with the second empty space V2, which is defined in the heat block 100, therebetween, and thus, total four discharge holes DH may be defined in the heat block 100. In general, when total $n^2$ reaction vessel accommodation spaces are defined in an n×n matrix form in the heat block of the gene amplification module according to the present invention, n−1 supply holes may be defined at each of two sidewalls defined at opposite sides with the first empty space of the heat block 100 therebetween, and thus, total 2×(n−1) supply holes may be defined in the heat block 100. Similarly, when total $n^2$ reaction vessel accommodation spaces are defined in an n×n matrix form in the heat block of the gene amplification module according to the present invention, n−1 discharge holes may be defined at each of two sidewalls defined at opposite sides with the second empty space of the heat block 100 therebetween, and thus, total 2×(n−1) discharge holes may be defined in the heat block 100.

As described above, in the heat block of the gene amplification module according to the present invention, total m×n reaction container communication spaces may be defined in an m×n matrix form (where m and n are natural numbers different from each other). In this case, m−1 supply holes may be defined in each of two sidewalls disposed at opposite sides with the first empty space of the heat block therebetween, and thus, total 2×(m−1) supply holes may be defined in the heat block. Also, n−1 discharge holes may be defined in each of two sidewalls disposed at opposite sides with the second empty space of the heat block therebetween, and thus, total 2×(n−1) discharge holes may be defined in the heat block.

When total m×n reaction container accommodation spaces are defined in an m×n matrix form in the heat block, this structure, in which the m−1 supply holes are defined in each of the two sidewalls disposed at the opposite sides with the first empty space of the heat block therebetween, and the n−1 discharge holes are defined in the two sidewall disposed at the opposite sides with the second empty space of the heat block therebetween, is because the supply holes SH and the discharge holes DH are respectively defined between the reaction container accommodation spaces R as illustrated in FIGS. 5 and 6.

Also, as illustrated in FIGS. 5 and 6, the supply holes SH defined at the opposite sides with the first empty space V1 therebetween and the discharge holes DH defined at the opposite sides with the second empty space V2 therebetween may communicate with the first empty space V1 and the second empty space V2, respectively.

Embodiment 1

A heat block having a length of 16 mm and a width of 16 mm was prepared. Each of four sidewalls of the heat block had a curved surface having a wave shape, and total four reaction container accommodation spaces were defined in a 2×2 matrix form in the heat block. Each of the reaction container accommodation spaces had a diameter of 4.5 mm. The heat block was made of aluminum.

Holes, each of which has a diameter of 4.8 mm, were defined one by one in the four sidewalls of the heat block, and an empty space having a cross (+) shape was defined in the heat block. The holes communicated with each other by the empty space.

A Peltier-based heating part that is thermoelectric element was provided below the heat block. The product name VT-127-1.4-1.15-71 manufactured by TE technology, INC, USA was used as the heating unit that is a thermoelectric element configured to heat the heat block by the Peltier effect.

A cooling part was disposed in close contact with a lower portion of the heating part. The cooling part was provided as a heat sink that is capable of absorbing heat. A blowing fan was installed on a lower end of the heat sink to reduce a temperature of the heat sink. the product name CTV-GF-04 manufactured by Coolertech of Korea was used as the heat sink and the blowing fan.

A fluid supply part was disposed in close contact with each of two sidewalls facing each other at opposite sides among the four sidewalls of the heat block. The fluid supply part was configured to supply a cooling fluid to the empty space of the heat block by driving the fan. The product name HFD 0200605 SEM, B-type manufactured by YeHAUS, China was used as the fan constituting the fluid supply part.

In Embodiment 1, the heating part operated under a voltage of 14.8 V and current of 5 A to heat the heat block until a temperature of the heat block reaches 95 degrees Celsius, and then, the operation of the heating part was stopped, and the fluid supply part operated under conditions of 11.1 V, 0.28 A, and 3.1 W until the temperature of the heat block reaches 60 degrees Celsius by the cooling fluid and the cooling part installed on the lower end. Particularly, in the cooling process, the blowing fan installed on the lower end of the heat sink operated to reduce a temperature of the heat sink, and thus, a gradient was generated between the heat block and the heat sink to cool the heat block. The heating and cooling processes were repeated.

Embodiment 2

Embodiment 2 was performed in the same manner as in Embodiment 1 except that the fluid supply part operated under conditions of 7.4 V, 0.21 V and 1.5 W to cool the heat block until the temperature of the heat block reaches 60 degrees Celsius.

Comparative Example

Comparative Example was performed in the same manner as in Embodiment 1 except that the fluid supply part is not provided.

Experimental Example

A time taken to complete thirty heating and cooling processes according to Embodiments and Comparative Example was measured.

In the case of Embodiment 1, it was taken 602 seconds to complete the thirty heating and cooling processes, and in the case of Embodiment 2, it was taken 674 seconds to complete the thirty heating and cooling processes. In the case of Comparative Example, it was taken 840 seconds to complete the thirty heating and cooling processes.

As seen from the experimental results, when the cooling fluid is supplied to the empty space of the heat block according to Embodiments 1 and 2, it may be confirmed that the time taken to complete the cooling and heat processes is significantly reduced when compared to the case in which the cooling fluid is not supplied. For example, in the case of Embodiment 1 in comparison to Comparative Example, it is confirmed that the time taken to complete the heating and cooling processes is reduced by about 30%.

While the embodiments of the present invention have been described with reference to the specific embodiments, it will be apparent to those skilled in the art that various changes and modifications may be made without departing from the spirit and scope of the invention as defined in the following claims.

The invention claimed is:

1. A gene amplification module comprising:
  a heat block having one or more reaction container accommodation spaces extending therein, the heat block made of a metal, each reaction container accommodation space being configured to accommodate a reaction container containing a specimen to be amplified, each reaction container accommodation space being a recess that extends from a top surface of the heat block toward a bottom surface of the heat block and has a predetermined length, the top and bottom surfaces of the heat block being flat, parallel, and opposite one another, the heat block having sidewalls having an outer circumference of the heat block and extending between the top surface and the bottom surface, the sidewalls having one or more supply holes extending therein, the supply holes configured to supply a cooling fluid to the heat block;

a heating part provided below the heat block, the heating part configured to heat the heat block by being heat-exchanged with the heat block through thermal conduction;

a cooling part provided below the heating part, the cooling part configured to cool the heat block by being heat-exchanged with the heating part through thermal conduction; and a fluid supply part facing one or more sides of the heat block, the fluid supply part being configured to supply the cooling fluid to the heat block, wherein the heat block has an empty space extending therein, and the empty space penetrates at least a portion of the heat block and is in fluid communication with the supply holes, and a portion of the heat block surrounding the empty space extends completely around each recess so that the empty space is not in fluid communication with the reaction container accommodation spaces.

2. The gene amplification module of claim 1, wherein, in the heat block, the one or more reaction container accommodation spaces include m×n reaction container accommodation spaces defined in an m×n matrix form (where m and n are natural numbers different from each other), or the one or more reaction container accommodation spaces include $n^2$ reaction container accommodation spaces defined in an n×n matrix form, and the supply holes are defined between the reaction container accommodation spaces, respectively.

3. The gene amplification module of claim 1, wherein the fluid supply part comprises:

a first fluid supply part provided to face a first sidewall of the heat block in which a first subset of the one or more supply holes are defined; and a second fluid supply part provided to face a second sidewall of the heat block in which a second subset of the one or more supply holes are defined.

4. The gene amplification module of claim 1, wherein the fluid supply part is in contact with the sidewalls having the one or more supply holes defined therein.

5. The gene amplification module of claim 1, wherein the empty space comprises:

a first empty space in fluid communication with the supply holes; and a second empty space in fluid communication with the first empty space.

6. The gene amplification module of claim 5, wherein the sidewalls have one or more discharge holes defined therein, the one or more discharge holes being in fluid communication with the second empty space.

7. The gene amplification module of claim 6, wherein the one or more discharge holes include a first discharge hole defined at a first end of the second empty space and a second discharge hole defined at a second end of the second empty space, the second end being opposite the first end.

8. The gene amplification module of claim 1, wherein the fluid supply part comprises a rotatable fan configured to supply the cooling fluid into the empty space of the heat block.

* * * * *